US009566747B2

(12) United States Patent
Romero et al.

(10) Patent No.: US 9,566,747 B2
(45) Date of Patent: Feb. 14, 2017

(54) METHOD OF MAKING AN ELECTRICAL STIMULATION LEAD

(71) Applicant: BOSTON SCIENTIFIC NEUROMODULATION CORPORATION, Valencia, CA (US)

(72) Inventors: Daniel James Romero, Newhall, CA (US); Joshua Dale Howard, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 325 days.

(21) Appl. No.: 14/332,212

(22) Filed: Jul. 15, 2014

(65) Prior Publication Data

US 2015/0021817 A1  Jan. 22, 2015

Related U.S. Application Data (60) Provisional application No. 61/856,996, filed on Jul. 22, 2013.

(51) Int. Cl.
   *B29C 45/14* (2006.01)
   *B29C 70/84* (2006.01)
   (Continued)

(52) U.S. Cl.
   CPC ............ *B29C 70/84* (2013.01); *A61N 1/0534* (2013.01); *B29C 45/14065* (2013.01);
   (Continued)

(58) Field of Classification Search
   None
   See application file for complete search history.

(56) References Cited

U.S. PATENT DOCUMENTS 4,602,624 A   7/1986   Naples et al.
4,630,611 A   12/1986  King
(Continued)

FOREIGN PATENT DOCUMENTS

EP   0580928 A1   2/1994
EP   0650694 B1   7/1998
(Continued)

OTHER PUBLICATIONS

U.S. Appl. No. 14/557,211, filed Dec. 1, 2014.
(Continued)

*Primary Examiner* — Edmund Lee
(74) *Attorney, Agent, or Firm* — Lowe Graham Jones PLLC; Bruce E. Black (57) ABSTRACT

A lead with segmented electrodes can be made using one or two mold methods. In one method, segmented electrodes are individually disposed on pins on an interior surface within a mold. Each of the segmented electrodes has at least one opening formed in the exterior surface of the segmented electrode. The lead body is then molded between the electrodes. In a two mold method, segmented electrodes are inserted into electrode slots of a first mold and an interior portion of a lead body is formed. The resulting intermediate arrangement is placed into a second mold to form an exterior portion of the lead body. In another two mold method, a sacrificial ring is formed around the segmented electrodes in a first mold and the resulting intermediate structure is inserted in a second mold to form the lead body. The sacrificial ring is then removed.

14 Claims, 7 Drawing Sheets

(51) Int. Cl.
*A61N 1/05* (2006.01)
*B29C 70/68* (2006.01)
B29K 101/12 (2006.01)
B29L 31/00 (2006.01)
B29C 33/12 (2006.01)

(52) U.S. Cl.
CPC .. *B29C 45/14467* (2013.01); *B29C 45/14639* (2013.01); *B29C 70/681* (2013.01); *A61N 1/0551* (2013.01); *B29C 33/12* (2013.01); *B29C 45/14811* (2013.01); *B29C 2045/1454* (2013.01); *B29C 2045/14122* (2013.01); *B29C 2045/14131* (2013.01); *B29K 2101/12* (2013.01); *B29K 2715/00* (2013.01); *B29K 2995/0005* (2013.01); *B29K 2995/0056* (2013.01); *B29L 2031/753* (2013.01); *B29L 2031/7546* (2013.01)

(56) References Cited

U.S. PATENT DOCUMENTS

| | | | |
|---|---|---|---|
| 4,744,370 A | 5/1988 | Harris | |
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,181,969 B1 | 1/2001 | Gord | |
| 6,322,559 B1 | 11/2001 | Daulton et al. | |
| 6,510,347 B2 | 1/2003 | Borkan | |
| 6,516,227 B1 | 2/2003 | Meadows et al. | |
| 6,556,873 B1 | 4/2003 | Smits | |
| 6,564,078 B1 | 5/2003 | Marino et al. | |
| 6,609,029 B1 | 8/2003 | Mann et al. | |
| 6,609,032 B1 | 8/2003 | Woods et al. | |
| 6,678,564 B2 | 1/2004 | Ketterl et al. | |
| 6,741,892 B1 | 5/2004 | Meadows et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,203,548 B2 | 4/2007 | Whitehurst et al. | |
| 7,244,150 B1 | 7/2007 | Brase et al. | |
| 7,292,890 B2 | 11/2007 | Whitehurst et al. | |
| 7,450,997 B1 | 11/2008 | Pianca et al. | |
| 7,489,971 B1 | 2/2009 | Franz | |
| 7,668,601 B2 | 2/2010 | Hegland et al. | |
| 7,672,734 B2 | 3/2010 | Anderson et al. | |
| 7,761,165 B1 | 7/2010 | He et al. | |
| 7,761,985 B2 | 7/2010 | Hegland et al. | |
| 7,783,359 B2 | 8/2010 | Meadows | |
| 7,792,590 B1 | 9/2010 | Pianca et al. | |
| 7,809,446 B2 | 10/2010 | Meadows | |
| 7,822,482 B2 | 10/2010 | Gerber | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,949,395 B2 | 5/2011 | Kuzma | |
| 7,974,705 B2 | 7/2011 | Zdeblick et al. | |
| 7,974,706 B2 | 7/2011 | Moffitt et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,175,710 B2 | 5/2012 | He | |
| 8,224,450 B2 | 7/2012 | Brase | |
| 8,225,504 B2 | 7/2012 | Dye et al. | |
| 8,271,094 B1 | 9/2012 | Moffitt et al. | |
| 8,295,944 B2 | 10/2012 | Howard et al. | |
| 8,321,025 B2 | 11/2012 | Bedenbaugh | |
| 8,359,107 B2 | 1/2013 | Pianca et al. | |
| 8,364,278 B2 | 1/2013 | Pianca et al. | |
| 8,391,985 B2 | 3/2013 | McDonald | |
| 8,583,237 B2 | 11/2013 | Bedenbaugh | |
| 8,688,235 B1 | 4/2014 | Pianca et al. | |
| 8,875,391 B2* | 11/2014 | Pianca | A61N 1/05 29/843 |
| 8,887,387 B2* | 11/2014 | Pianca | A61N 1/0534 29/847 |
| 9,005,503 B2* | 4/2015 | Govea | A61N 1/05 264/261 |
| 9,089,689 B2* | 7/2015 | Govea | A61N 1/0534 |
| 2001/0023368 A1 | 9/2001 | Black et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0150036 A1 | 6/2007 | Anderson | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 | 10/2008 | Jensen et al. | |
| 2009/0054941 A1 | 2/2009 | Eggen et al. | |
| 2009/0187222 A1 | 7/2009 | Barker | |
| 2009/0204192 A1 | 8/2009 | Carlton et al. | |
| 2009/0276021 A1 | 11/2009 | Meadows et al. | |
| 2010/0030298 A1 | 2/2010 | Martens et al. | |
| 2010/0036468 A1 | 2/2010 | Decre et al. | |
| 2010/0076535 A1 | 3/2010 | Pianca et al. | |
| 2010/0077606 A1 | 4/2010 | Black et al. | |
| 2010/0082076 A1 | 4/2010 | Lee et al. | |
| 2010/0094387 A1 | 4/2010 | Pianca et al. | |
| 2010/0100152 A1 | 4/2010 | Martens et al. | |
| 2010/0268298 A1 | 10/2010 | Moffitt et al. | |
| 2010/0269338 A1 | 10/2010 | Dye | |
| 2010/0269339 A1 | 10/2010 | Dye et al. | |
| 2010/0287770 A1 | 11/2010 | Dadd et al. | |
| 2011/0004267 A1 | 1/2011 | Meadows | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0077699 A1 | 3/2011 | Swanson et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0238129 A1 | 9/2011 | Moffitt et al. | |
| 2011/0245903 A1 | 10/2011 | Schulte et al. | |
| 2011/0301665 A1 | 12/2011 | Mercanzini et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1* | 8/2012 | DiGiore | A61N 1/0534 607/148 |
| 2012/0203321 A1 | 8/2012 | Moffitt et al. | |
| 2012/0316615 A1 | 12/2012 | DiGiore et al. | |
| 2013/0105071 A1 | 5/2013 | DiGiore et al. | |
| 2013/0109254 A1 | 5/2013 | Klardie et al. | |

(56) References Cited

U.S. PATENT DOCUMENTS

| | | |
|---|---|---|
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0088666 A1 | 3/2014 | Goetz et al. |
| 2014/0142671 A1 | 5/2014 | Moffitt et al. |
| 2014/0167317 A1* | 6/2014 | Govea ............... B29C 45/14639 264/261 |
| 2014/0180375 A1 | 6/2014 | Pianca et al. |
| 2015/0142090 A1* | 5/2015 | Duijsens .................. A61N 1/05 607/116 |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/286,889, filed May 23, 2014.
U.S. Appl. No. 14/286,934, filed May 23, 2014.
U.S. Appl. No. 14/286,829, filed May 23, 2014.
U.S. Appl. No. 14/286,940, filed May 23, 2014.
U.S. Appl. No. 14/325,249, filed Jul. 7, 2014.
U.S. Appl. No. 14/452,461, filed Aug. 5, 2014.
U.S. Appl. No. 14/286,797, filed May 23, 2014.
U.S. Appl. No. 14/469,214, filed Aug. 26, 2014.
International Search Report and Written Opinion for PCT/US2014/046749 mailed Sep. 30, 2014.

* cited by examiner

METHOD OF MAKING AN ELECTRICAL STIMULATION LEAD

CROSS-REFERENCE TO RELATED APPLICATIONS

This application claims the benefit under 35 U.S.C. §119(e) of U.S. Provisional Patent Application Ser. No. 61/856,996, filed Jul. 22, 2013, which is incorporated herein by reference.

FIELD

The present invention is directed to the area of implantable electrical stimulation systems and methods of making and using the systems. The present invention is also directed to implantable electrical stimulation leads having segmented electrodes, as well as methods of making and using the leads and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a method of making an electrical stimulation lead. The method includes individually disposing segmented electrodes on pins disposed on an interior surface within a mold. Each of the segmented electrodes has at least one opening formed in the exterior surface of the segmented electrode to receive at least one of the pins so that the segmented electrodes can be positioned in a predetermined arrangement within the mold with the segmented electrodes spaced apart from each other. The method further includes attaching a conductor wire to each of the segmented electrodes; molding a lead body between the segmented electrodes disposed in the mold; and removing the lead body, segmented electrodes, and conductors from the mold.

Another embodiment is a method of making an electrical stimulation lead. The method includes individually inserting segmented electrodes into electrode slots formed on an interior surface within a first mold; attaching a conductor wire to each of the segmented electrodes; molding an interior portion of a lead body between the segmented electrodes disposed in the first mold to form an intermediate arrangement; removing the intermediate arrangement from the first mold; placing the intermediate arrangement into a second mold; and molding an exterior portion of the lead body over the interior portion of the lead body and between the segmented electrodes within the second mold.

Yet another embodiment is a method of making an electrical stimulation lead. The method includes individually inserting segmented electrodes into a central cylinder of a first mold and within an outer body of the first mold; forming a sacrificial ring around the segmented electrodes and in adhering contact with an outer surface of the segmented electrodes to form an intermediate structure; inserting the intermediate structure into a second mold; attaching a conductor wire to each of the segmented electrodes; molding a lead body between the segmented electrodes disposed in the second mold; removing the segmented electrodes and lead body from the second mold; and removing the sacrificial ring to expose the outer surfaces of the segmented electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having segmented electrodes, as well as methods of making and using the leads and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and U.S. patent applications Ser. Nos. 12/177,823; 13/667,953; and 13/750,725, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

Figure 1:
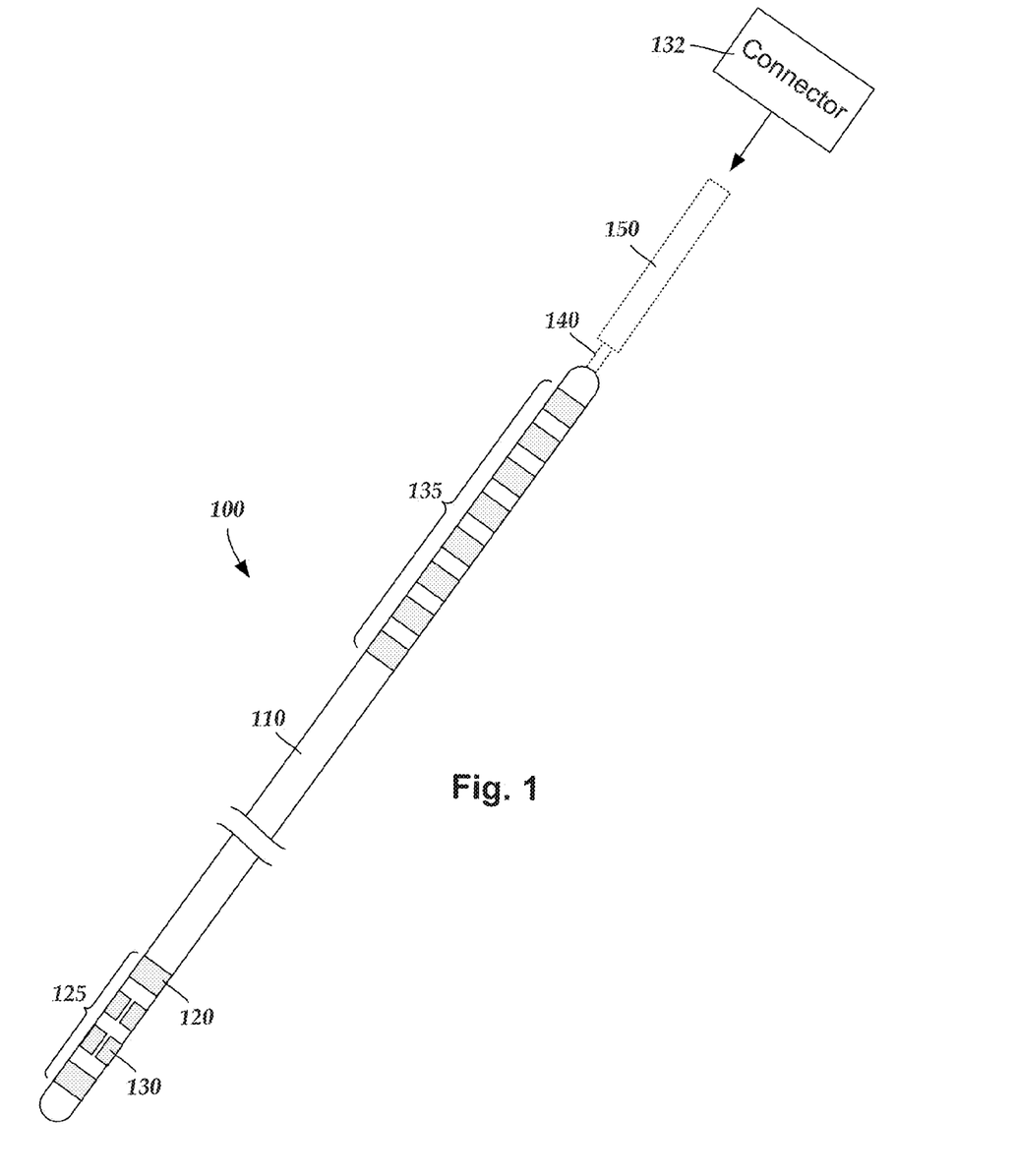
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more or fewer than eight stimulation channels (e.g., 4-, 6-, 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 may be disposed on any part of the lead body 110, usually near a distal end of the lead 100. In FIG. 1, the lead 100 includes two ring electrodes 120. Any number of ring electrodes 120 may be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes may be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see, e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

In FIG. 1, the lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two sets of ring electrodes 120 and two sets of segmented electrodes 130, the ring electrodes 120 can flank the two sets of segmented electrodes 130 (see e.g., FIG. 1). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figure 3A:
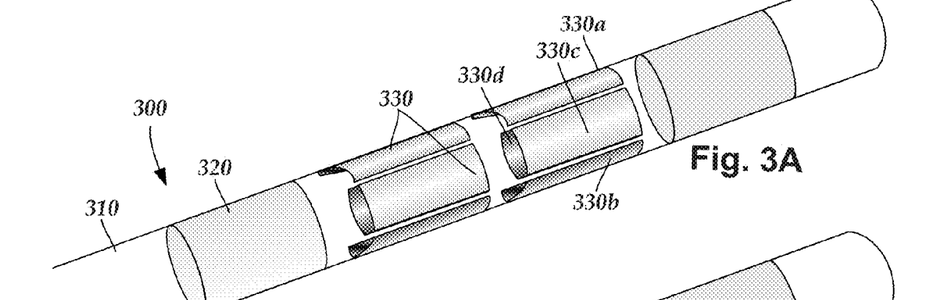
FIG. 3A is a schematic perspective view of an embodiment of a portion of a lead having a plurality of segmented electrodes, according to the invention.
Figures 3B, 3C:
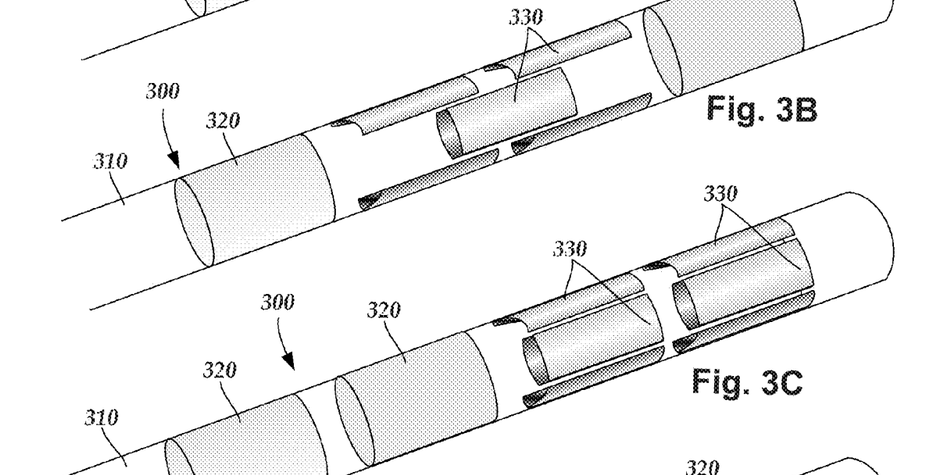
FIG. 3B is a schematic perspective view of a second embodiment of a portion of a lead having a plurality of segmented electrodes, according to the invention.
FIG. 3C is a schematic perspective view of a third embodiment of a portion of a lead having a plurality of segmented electrodes, according to the invention.
Figure 3D:
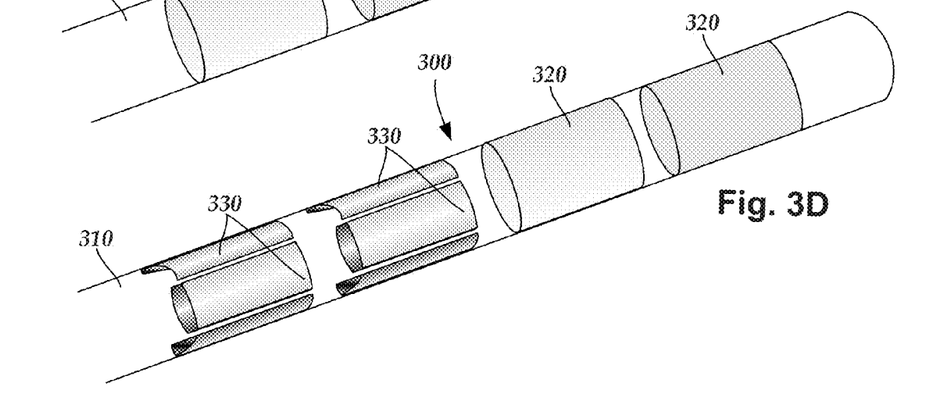
FIG. 3D is a schematic perspective view of a fourth embodiment of a portion of a lead having a plurality of segmented electrodes, according to the invention.
Figures 3E, 3F:
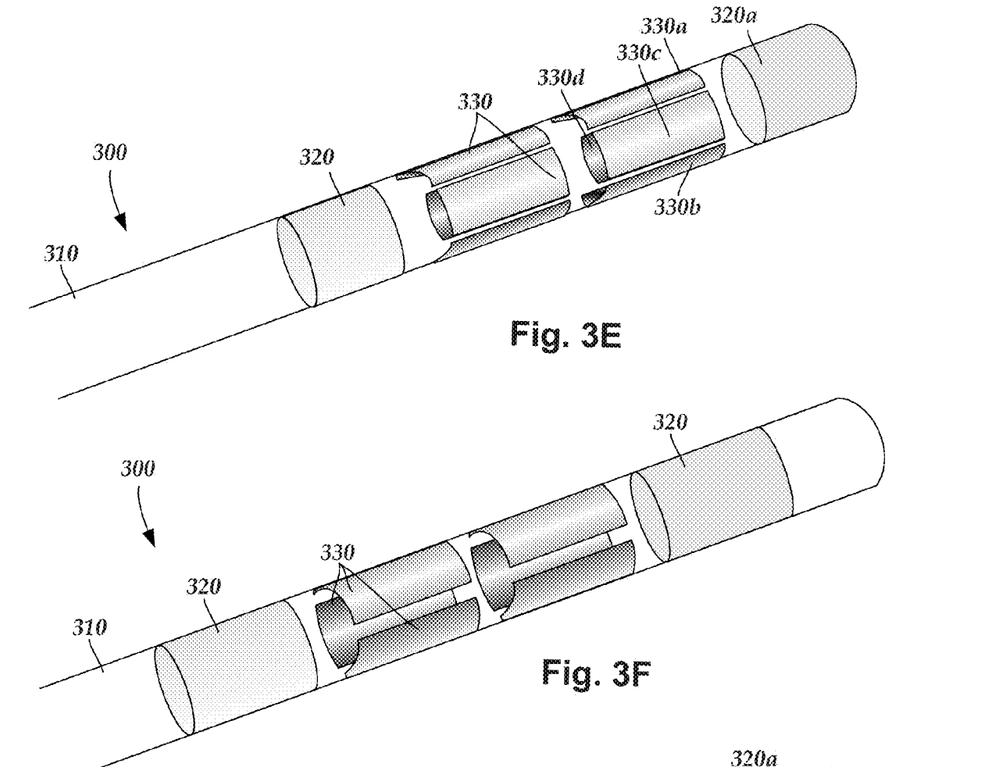
FIG. 3E is a schematic perspective view of a fifth embodiment of a portion of a lead having a plurality of segmented electrodes, according to the invention.
FIG. 3F is a schematic perspective view of a sixth embodiment of a portion of a lead having a plurality of segmented electrodes, according to the invention.
Figure 3G:
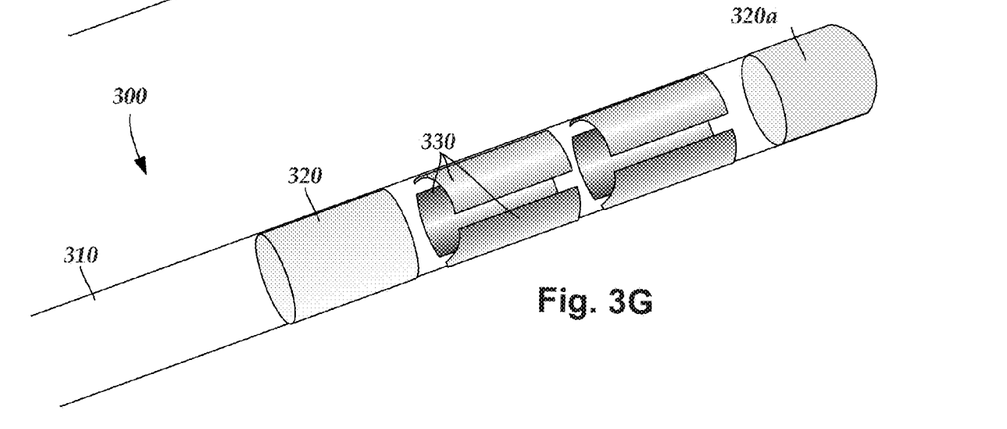
FIG. 3G is a schematic perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F and 3G can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F and 3G has two sets of segmented electrodes, each set containing three electrodes disposed around the circumference of the lead, flanked by two ring electrodes (FIG. 3F) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
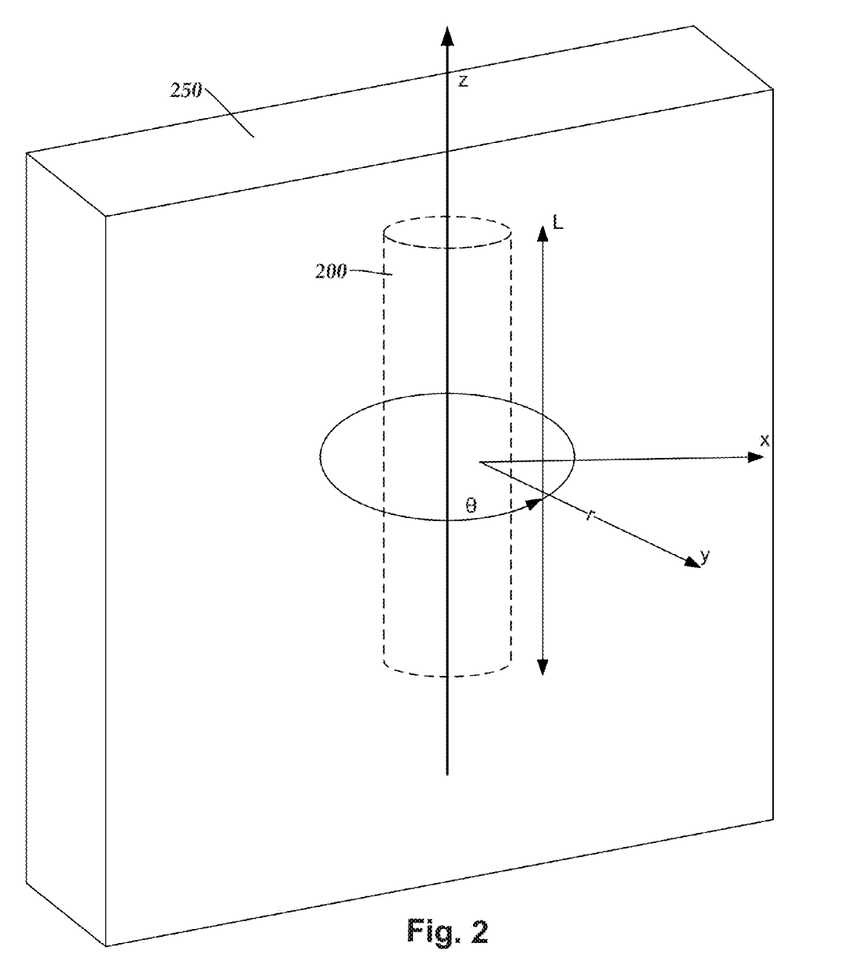
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see, FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3E illustrate leads 300 with segmented electrodes 330, optional ring electrodes 320 or tip electrodes 320a, and a lead body 310. The sets of segmented electrodes 330 include either two (FIG. 3B) or four (FIGS. 3A, 3C, and 3D) or any other number of segmented electrodes including, for example, three, five, six, or more.

Any other suitable arrangements of segmented electrodes can be used. As an example, arrangements in which segmented electrodes are arranged helically with respect to each other. One embodiment includes a double helix.

One challenge to making leads with segmented electrodes is the correct placement of the electrodes, and retention of the desired electrode placement, during the manufacturing process. A number of methods for manufacturing a lead with segmented electrodes have been developed using a mold to position the segmented electrodes in the desired arrangement during formation of the lead body.

Figure 4A:
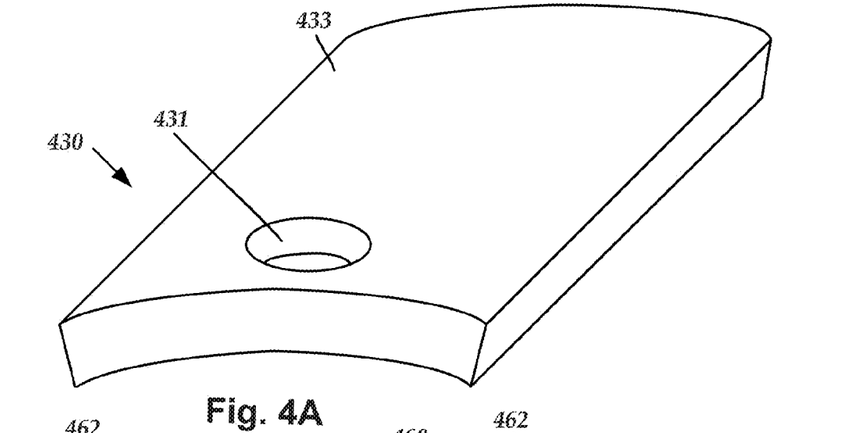
FIG. 4A is a schematic perspective view of one embodiment of a segmented electrode, according to the invention.

FIGS. 4A-4D illustrate methods of forming a lead with segmented electrodes using a mold with pins for placement of the segmented electrodes. FIG. 4A illustrates a segmented electrode 430 with an opening 431 formed in an exterior surface 433 of the segmented electrode. The segmented electrodes 430 can be formed using any suitable methods, including, but not limited to, machining, molding, stamping, and the like. The opening 431 may pass through the entire thickness of the segmented electrode 430 or the opening may only extend partially through the thickness of the segmented electrode. The opening 431 may be positioned anywhere on the exterior surface 433 of the segmented electrode 430. In at least some embodiments, for an array of segmented electrodes, the openings will all be positioned at the same place on all of the segmented electrodes. It will also be understood that, although a single opening is illustrated in FIG. 4A, a segmented electrode could have two or more openings.

Figure 4B:
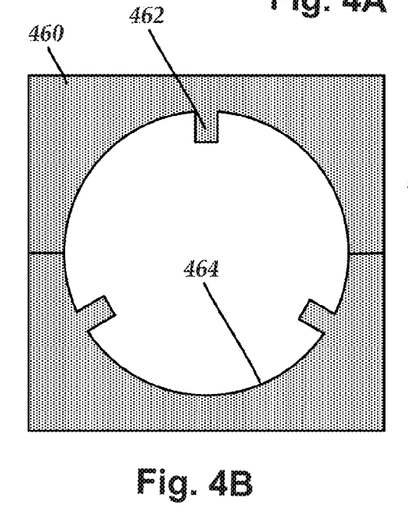
FIG. 4B is a schematic cross-sectional view of one embodiment of a mold for use with the segmented electrode of FIG. 4A, according to the invention.

FIG. 4B illustrates, in cross-section, a mold 460 for use in forming the lead. The mold 460 includes pins 462 that extend from an interior surface 464 of the mold. The pins 462 can be specifically arranged in the mold for a desired segmented electrode arrangement or there may be an array of pins from which a user can select to produce the desired segmented electrode arrangement. The mold 460 may be formed in two or more pieces, as illustrated in FIG. 4B, and the pieces may be entirely separate or coupled together by a hinge or other mechanism.

Figure 4C:
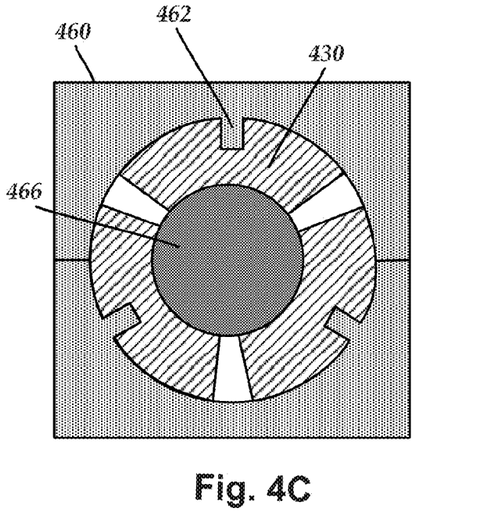
FIG. 4C is a schematic cross-sectional view of the segmented electrodes of FIG. 4A inserted into the mold of FIG. 4B, according to the invention.

The segmented electrodes 430 are disposed in the mold 460 with the pins 462 of the mold received in the openings 431 of the segmented electrodes, as illustrated in FIG. 4C. In some embodiments, the pins 462 and openings 431 have a friction fit that facilitates retention of the segmented electrodes 430 on the pins 462. In other embodiments, the segmented electrodes 430 and the pins 462 have a looser fit to facilitate removal of the segmented electrodes from the mold after molding the lead body.

In some embodiments, a cylindrical body 466, such as a tube or mandrel, is inserted between the segmented electrodes 430 to hold the electrodes in place against the interior surface 464 of the mold 460. If a tube is used, the lumen of the tube may be used as a stylet lumen during implantation of the lead or may be used to deliver medication to the tissue after implantation or any combination thereof.

The mold 460 is illustrated in cross-section, but it will be understood that there may be multiple sets of segmented electrodes disposed at different longitudinal positions along the mold. In addition, one or more ring or tip electrodes may also be inserted into the mold.

In at least some embodiments, a conductor is attached to each segmented electrode (and any ring or tip electrodes) prior to molding. The lead body is then molded between the segmented electrodes (and any ring or tip electrodes). The lead body is generally formed of a biocompatible, non-conductive material. Any suitable method of molding can be used including, but not limited to, injection molding. Leads with electrode arrangements such as those illustrated in FIGS. 3A-3G can be formed using a mold 460 with pins 462 positioned along the mold in the desired segmented electrode arrangement.

In at least some embodiments, the tolerances of the pins and openings are selected so that no (or very little) material of the lead body flows over the exterior surface 433 of the segmented electrodes 430. In at least some embodiments, a diameter of the cylindrical body 466 is selected so that no (or very little) material of the lead body flows over the exterior surface 433 of the segmented electrodes 430. If, however, any material of the lead body extends over the exterior surface 433 of the segmented electrodes 430, such material (often referred to as "flash") can be removed by any suitable technique including, but not limited to, cutting, scraping, laser ablation or cutting, grinding, and the like. A lead may also be subjected to grinding, such as centerless grinding, to ensure that the lead body is isodiametric, particularly along its distal end.

In at least some embodiments, the openings 431 in the segmented electrodes 430 are filled after forming the lead body. Any suitable biocompatible material can be used to fill the openings including, but not limited to, metal, epoxy, or plastic.

Figures 5A, 5B, 5C:
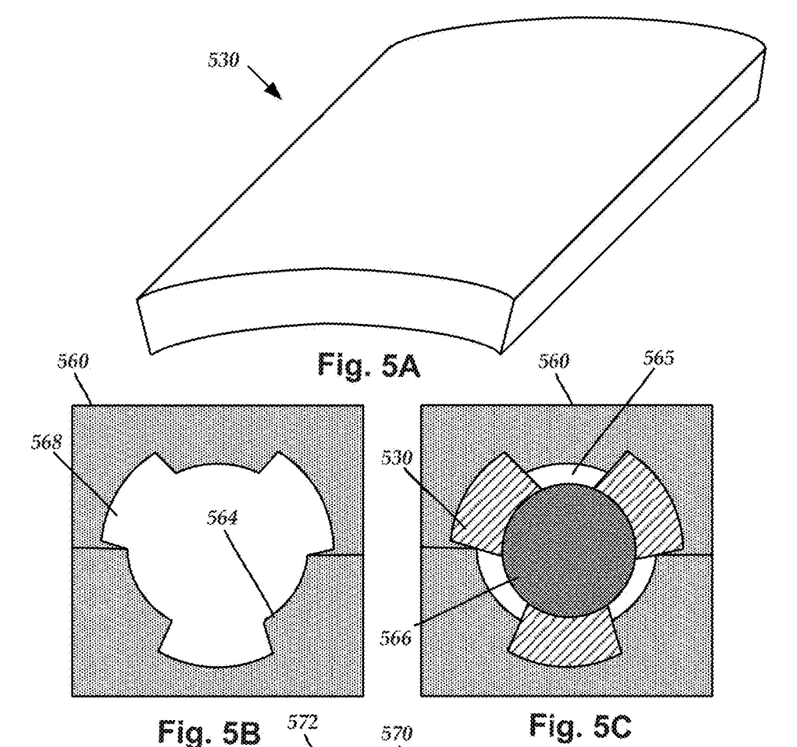
FIG. 5A is a schematic perspective view of another embodiment of a segmented electrode, according to the invention.
FIG. 5B is a schematic cross-sectional view of one embodiment of a first mold for use with the segmented electrode of FIG. 5A, according to the invention.
FIG. 5C is a schematic cross-sectional view of the segmented electrodes of FIG. 5A inserted into the first mold of FIG. 5B, according to the invention.

In other methods, a two step molding process can be used with electrode slots formed in the first mold. FIGS. 5A-5F illustrate such a method of forming a lead with segmented electrodes. FIG. 5A illustrates a segmented electrode 530. The segmented electrodes 530 can be formed using any suitable methods, including, but not limited to, machining, molding, stamping, and the like. FIG. 5B illustrates a first mold 560 with a set of electrode slots 568 formed on the interior surface 564 of the first mold. The segmented electrodes 530 are inserted into the electrode slots of the first mold 560, as illustrated in FIG. 5C. A portion of each of the electrodes 530 extends into the central lumen 565 of the first mold 560. In at least some embodiments, the portion of the electrode 530 that extends into the central lumen 565 is at least 25%, 30%, 40%, 50%, 60%, or 70% of the thickness of the electrode 530.

In some embodiments, the electrodes 530 and electrode slots 568 have a friction fit that facilitates retention of the segmented electrodes 530 in the electrode slots. In other embodiments, the segmented electrodes 430 and the electrode slots 568 have a looser fit to facilitate removal of the segmented electrodes 430 from the first mold 560 after molding. In some embodiments, a cylindrical body 566, such as a tube or mandrel, is inserted between the segmented electrodes 530 to hold the electrodes in place against the interior surface 564 of the first mold 560. If a tube is used, the lumen of the tube may be used as a stylet lumen during implantation of the lead.

The first mold 560 is illustrated in cross-section, but it will be understood that there may be multiple sets of segmented electrodes disposed at different longitudinal positions along the first mold. In addition, one or more ring or tip electrodes may also be inserted into the first mold.

Figure 5D:
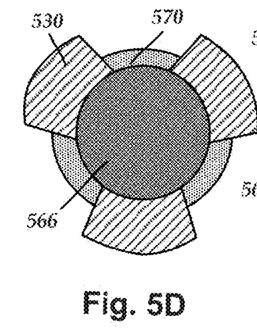
FIG. 5D is a schematic cross-sectional view of one embodiment of an intermediate arrangement of the segmented electrodes of FIG. 5A and an interior portion of a lead body formed by molding using the first mold of FIG. 5B, according to the invention.

Typically, a conductor is attached to each segmented electrode (and any ring or tip electrodes) prior to molding. An interior portion 570 of the lead body is then molded between the segmented electrodes 530 (and any ring or tip electrodes) and an intermediate arrangement formed of the segmented electrodes and interior portion of the lead body is removed from the first mold 560, as illustrated in FIG. 5D.

Figure 5E:
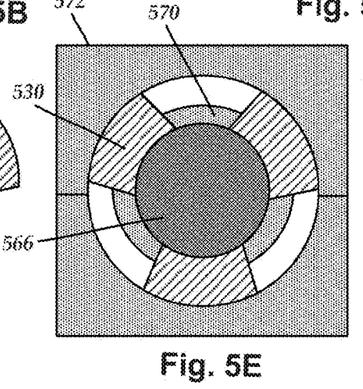
FIG. 5E is a schematic cross-sectional view of the intermediate arrangement of FIG. 5D inserted into a second mold, according to the invention.

This intermediate arrangement of segmented electrodes 530 (and any ring or tip electrodes) and interior portion 570 of the lead body is placed in a second mold 572, as illustrated in FIG. 5E. In at least some embodiments, the diameter of the central lumen of the second mold 572 is selected so that the outer surfaces of the segmented electrodes 530 fit snugly against the mold 572.

Figure 5F:
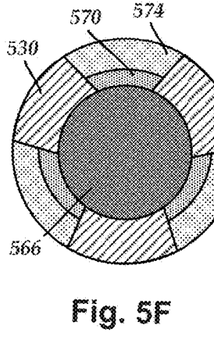
FIG. 5F is a schematic cross-sectional view of one embodiment of a lead containing the segmented electrodes of FIG. 5A, an interior portion of a lead body formed by molding using the first mold of FIG. 5B, and an exterior portion of a lead body formed by molding using the second mold of FIG. 5E, according to the invention.

An exterior portion of the lead body 574 is then molded between the segmented electrodes (and any ring or tip electrodes) and the lead is removed from the second mold, as illustrated in FIG. 5F. The materials used for the interior portion 570 and exterior portion 574 of the lead body can be the same or different.

In at least some embodiments, the tolerances of the segmented electrodes and second mold 572 are selected so that no (or very little) material of the lead body flows over the exterior surface of the segmented electrodes 530. If, however, any material of the lead body extends over the exterior surface of the segmented electrodes 530, such material (often referred to as "flash") can be removed by any suitable technique including, but not limited to, cutting, scraping, laser ablation or cutting, grinding, and the like. A lead may also be subjected to grinding, such as centerless grinding, to ensure that the lead body is isodiametric, particularly along its distal end.

Figure 6A:
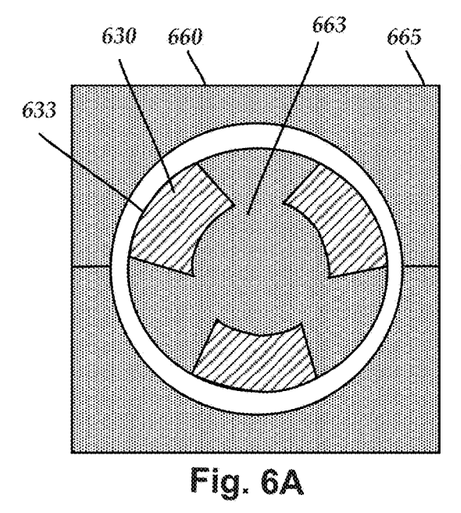
FIG. 6A is a schematic cross-sectional view of one embodiment of a first mold with segmented electrodes disposed in a central cylinder of the first mold, according to the invention.

Another method of forming a segmented electrode lead includes molding the segmented electrodes onto a sacrificial ring and then forming the lead body using a separate mold. FIGS. 6A-6D illustrate one embodiment of such a method. FIG. 6A illustrates a first mold 660 with a central cylinder 663 and an outer body 665. The central cylinder 663 has a set of electrode slots into which the segmented electrodes 630 are inserted, as illustrated in FIG. 6A. In at least some embodiments, the central cylinder 663 and segmented electrode 630 are arranged so that an upper surface 633 of the segmented electrodes is isodiametric, or depressed, with respect to adjacent portions of the central cylinder. The segmented electrodes 630 can be formed using any suitable methods, including, but not limited to, machining, molding, stamping, and the like.

Figure 6B:
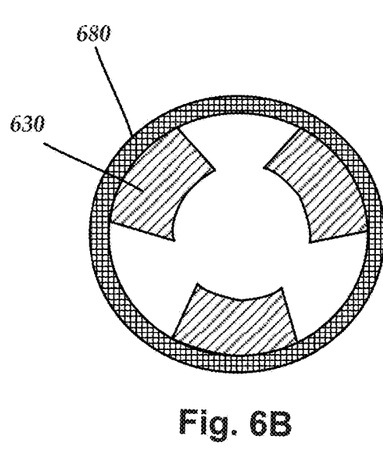
FIG. 6B is a schematic cross-sectional view of one embodiment of an intermediate arrangement of the segmented electrodes and a sacrificial ring formed by molding using the first mold of FIG. 6A, according to the invention.

A sacrificial ring 680 is molded around the segmented electrodes 530 and an intermediate arrangement formed of the segmented electrodes and sacrificial ring is removed from the first mold 660, as illustrated in FIG. 6B. Preferably, the sacrificial ring 680 only contacts the upper surface 633 of the segmented electrodes 630 (and any ring or tip electrodes), but this is not necessarily required. The sacrificial ring 680 is made of a rigid or hard plastic material that will retain its shape during subsequent processing. The material of the sacrificial ring 680 should also adhere to the segmented electrodes 630 sufficiently so that the segmented electrodes do not lose contact with the sacrificial ring until the second molding, described below. Preferably, the material of the sacrificial ring is biocompatible, particularly if there is a possibility of contamination of the lead body or segmented electrode with the remnants of the sacrificial ring.

The first mold 660 may be used with a single set of segmented electrodes or the first mold may accommodate multiple sets of segmented electrodes. In at least some embodiments, each set of segmented electrodes 630 will have its own sacrificial ring 680 that is not coupled or attached to the sacrificial ring of any other set of segmented electrodes. Thus, the sets of segmented electrodes are molded separately to the sacrificial ring so that the central cylinder can be easily removed, leaving behind the segmented electrodes 630 and sacrificial ring 680.

Figure 6C:
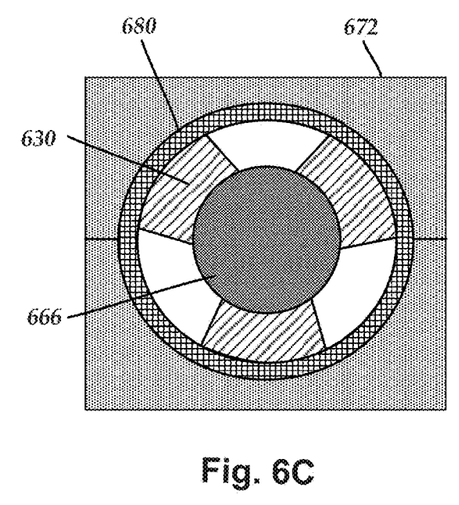
FIG. 6C is a schematic cross-sectional view of the intermediate arrangement of FIG. 6B inserted into a second mold, according to the invention.

This intermediate arrangement(s) of segmented electrodes 630 and sacrificial ring 680 is placed in a second mold 672, as illustrated in FIG. 6C. The inner diameter of the second mold 672, at the position of the segmented electrodes 630, should accommodate the sacrificial ring 680. Elsewhere in the mold, in at least some embodiments, the inner diameter will correspond to the desired outer diameter of the lead.

In addition, any ring or tip electrodes to be incorporated into the lead are also placed in the second mold 672. The inner diameter of the second mold 672 at the position of the ring or tip electrode should be the same, or nearly the same, as the outer diameter of the ring or tip electrode.

In at least some embodiments, a cylindrical body 766, such as a tube or mandrel, is inserted between the segmented electrodes 730. If a tube is inserted between the segmented electrodes, the lumen of the tube may be used as a stylet lumen during implantation of the lead or may be used to deliver medication to the tissue after implantation or any combination thereof.

Figure 6D:
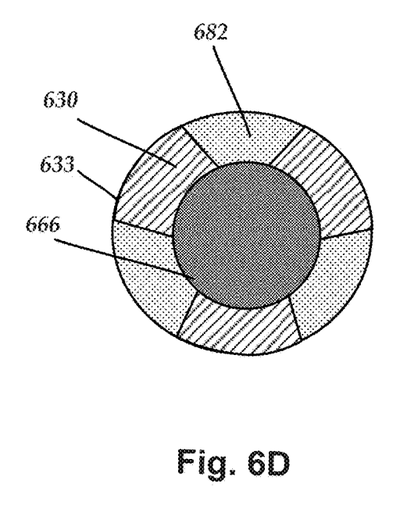
FIG. 6D is a schematic cross-sectional view of one embodiment of a lead containing segmented electrodes of FIG. 5A and a lead body formed by molding using the second mold of FIG. 6C, according to the invention.

The lead body 682 is then molded between the segmented electrodes (and any ring or tip electrodes) and the lead is removed from the second mold and the sacrificial ring 680 is removed to expose the outer surfaces 633 of the segmented electrodes 630, as illustrated in FIG. 6D. Removal of the sacrificial ring 680 can be performed using any suitable method including, but not limited to, cutting, scraping, peeling, pulling, grinding, dissolving, and the like or any combination thereof.

The above specification, examples and data provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A method of making an electrical stimulation lead, the method comprising:
    individually disposing a plurality of segmented electrodes on a plurality of pins disposed on an interior surface within a mold, wherein each of the segmented electrodes has at least one opening formed in an exterior surface of the segmented electrode to receive at least one of the pins so that the segmented electrodes can be positioned in a predetermined arrangement within the mold with the segmented electrodes spaced apart from each other;
    attaching a conductor wire to each of the segmented electrodes;
    molding a lead body between the segmented electrodes disposed in the mold; and
    removing the lead body, segmented electrodes, and conductors from the mold.

2. The method of claim 1, further comprising, prior to molding the lead body, inserting a cylindrical body into the mold to hold the segmented electrodes against the interior surface of the mold.

3. The method of claim 2, wherein the cylindrical body is a tube with a central lumen.

4. The method of claim 1, further comprising placing at least one ring electrode or tip electrode in the mold, wherein molding a lead body further comprises molding the lead body between the segmented electrodes and the at least one ring electrode or tip electrode.

5. The method of claim 1, wherein individually disposing a plurality of segmented electrodes comprises forming at least one set of segmented electrodes from the plurality of segmented electrodes, wherein the segmented electrodes of each set are distributed circumferentially around the mold at a same longitudinal position within the mold.

6. The method of claim 1, further comprising, after removal from the mold, filling the at least one opening in the segmented electrodes.

7. A method of making an electrical stimulation lead, the method comprising:
    individually inserting a plurality of segmented electrodes into a plurality of electrode slots formed on an interior surface within a first mold;
    attaching a conductor wire to each of the segmented electrodes;
    molding an interior portion of a lead body between the segmented electrodes disposed in the first mold to form an intermediate arrangement;
    removing the intermediate arrangement from the first mold;
    placing the intermediate arrangement into a second mold; and
    molding an exterior portion of the lead body over the interior portion of the lead body and between the segmented electrodes within the second mold.

8. The method of claim 7, wherein the interior portion and the exterior portion are formed of different materials.

9. The method of claim 7, further comprising, prior to molding the interior portion of lead body, inserting a cylindrical body into the first mold to hold the segmented electrodes against the interior surface of the first mold.

10. The method of claim 9, wherein the cylindrical body is a tube with a central lumen.

11. The method of claim 7, wherein each electrode slot of the first mold defines at least one slot extension extending into an adjacent part of the first mold and each of the segmented electrodes comprises at least one electrode extension, and wherein inserting a plurality of segmented electrodes comprises inserting the at least one electrode extension of the segmented electrodes into the at least one slot extensions of the electrode slots of the first mold.

12. The method of claim 11, wherein each electrode slot has two opposing slot extensions.

13. The method of claim 7, further comprising placing at least one ring electrode or tip electrode in the first mold, wherein molding an interior portion of a lead body further comprises molding the interior portion of the lead body between the segmented electrodes and the at least one ring electrode or tip electrode.

14. The method of claim 7, wherein individually inserting a plurality of segmented electrodes comprises forming at least one set of segmented electrodes from the plurality of segmented electrodes, wherein the segmented electrodes of each set are distributed circumferentially around the first mold at a same longitudinal position within the first mold.

* * * * *